(12) United States Patent
Peterson

(10) Patent No.: US 8,354,546 B2
(45) Date of Patent: Jan. 15, 2013

(54) PROCESS FOR MANUFACTURE OF OPTICALLY ACTIVE 2-(ACYLOXYMETHYL)-1,3-OXATHIOLANES

(75) Inventor: John R. Peterson, Chardon, OH (US)

(73) Assignee: Vertichem Corporation, Cambridge, Ontario (CA)

( * ) Notice: Subject to any disclaimer, the term of this patent is extended or adjusted under 35 U.S.C. 154(b) by 0 days.

(21) Appl. No.: 13/403,255

(22) Filed: Feb. 23, 2012

(65) Prior Publication Data

US 2012/0157693 A1 Jun. 21, 2012

Related U.S. Application Data

(62) Division of application No. 12/634,990, filed on Dec. 10, 2009, now Pat. No. 8,153,416.

(60) Provisional application No. 61/121,330, filed on Dec. 10, 2008.

(51) Int. Cl.
*C07D 327/04* (2006.01)
(52) U.S. Cl. .......................................... 549/30
(58) Field of Classification Search ............... 549/30
See application file for complete search history.

(56) References Cited

U.S. PATENT DOCUMENTS

| | | | |
|---|---|---|---|
| 4,619,931 A | 10/1986 | Heeres et al. | |
| 5,990,139 A | 11/1999 | Yano et al. | |
| 6,979,561 B1 | 12/2005 | Almond et al. | |
| 2005/0239795 A1 | 10/2005 | Neustadt et al. | |

FOREIGN PATENT DOCUMENTS

WO WO 95/29176 11/1995

OTHER PUBLICATIONS

International Preliminary Report on Patentability, Sep. 9, 2011, eleven pages.
International Search Report, Sep. 24, 2010.
Written Opinion, Sep. 24, 2010, nine pages.
International Search Report, Aug. 19, 2010, six pages.
Written Opinion, Aug. 19, 2010, nine pages.
Invitation to Pay Additional Fees, Aug. 4, 2010, five pages.
Michael R. Wood et al., "Benzodiazepines as Potent and Selective Bradykinin B1 Antagonists," Journal of Medicinal Chemistry, vol. 46, No. 10, pp. 1803-1806, 2003.
Partial International Search, Jul. 1, 2010, five pages.
Rick P.C. Cousins et al., "Enzymic Resolution of Oxathiolane Intermediates—An Alternative Approach to the Anti-viral Agent Lamivudine (#TC<TM>)," Tetrahedron: Asymmetry, vol. 6, No. 2, pp. 393-396, Feb. 1, 1995.
Romualdo Caputo, et al., "A New Strategy for the Asymmetric Synthesis of 1,3-Oxathiolane-Based Nucleoside Analogues," European Journal of Organic Chemistry, pp. 1455-1458, Jan. 1, 1999.
Tarek S. Mansour, et al., "Anti-Human Immunodeficiency Virus and Anti-Hepatitis-B virus Activities and Toxicities of the Enantiomers of 2'-Deoxy-3'-oxa-4'thiocytidine and Their 5-Fluoro Analogues in Vitro," Journal of Medicinal Chemistry, American Chemical Society, vol. 38, No. 1, pp. 1-4, Jan. 6, 1995.

*Primary Examiner* — Kristin Bianchi
(74) *Attorney, Agent, or Firm* — Brouse McDowell; Heather M. Barnes; Jennifer L. Hanzlicek

(57) ABSTRACT

There is provided a process for manufacture of optically-active, 2-(acyloxymethyl)-1,3-oxathiolanes of Formula I comprising a preparation of a racemic compound and an enzyme-catalyzed kinetic resolution of the enantiomers. The invention may further provide for the esterification and racemization of the by-product of the enzymatic reaction. In this manner, 2(R)-(benzoyloxymethyl)-1,3-oxathiolane is prepared as a useful intermediate for manufacture of the anti-HIV drug Apricitabine.

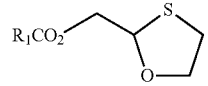

Formula I

15 Claims, 4 Drawing Sheets

PROCESS FOR MANUFACTURE OF OPTICALLY ACTIVE 2-(ACYLOXYMETHYL)-1,3-OXATHIOLANES

This divisional patent application claims priority from a utility patent application having Ser. No. 12/634,990, which was filed on Dec. 10, 2009 now U.S. Pat. No. 8,153,416, which claims priority from a provisional application having Ser. No. 61/121,330 filed on Dec. 10, 2008, which is incorporated herein by reference.

I. BACKGROUND OF THE INVENTION

A. Field of Invention

This invention pertains to a process for manufacture of optically active 2-(acyloxymethyl)-1,3-oxathiolanes of Formula I. Such products are useful intermediates in the manufacture of Apricitabine and related compounds.

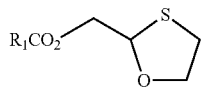

Formula I

B. Description of the Related Art

The 1,3-oxathiolane nucleosides comprise a clinically-important class of drugs for the treatment of human immunodeficiency virus (HIV), the etiologic agent responsible for the development of acquired immune deficiency syndrome in humans. Unlike the antecedent antivirals Abacavir, Didanosine, Stavudine, Tenofovir Disoproxil, Zalcitabine and Zidovudine, a 1,3-oxathiolane nucleoside hosts a pentacyclic thioacetal in place of a deoxyribose moiety.

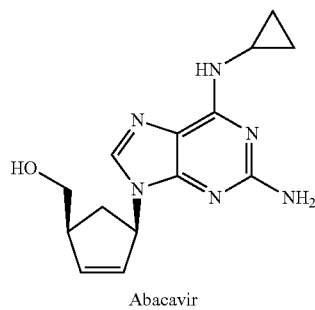

Abacavir

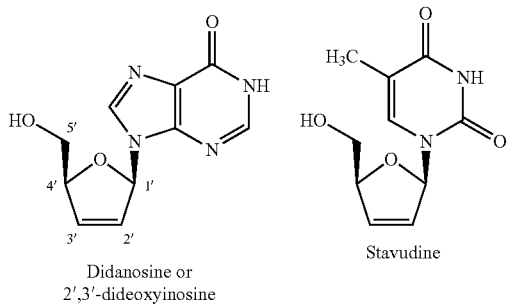

Didanosine or 2′,3′-dideoxyinosine

Stavudine

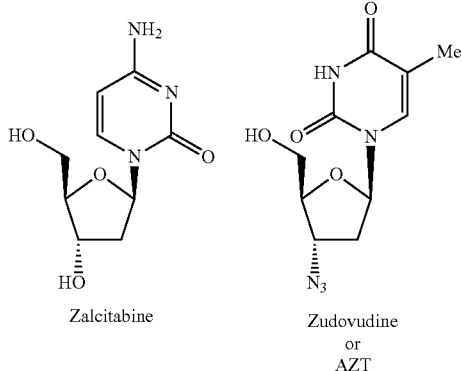

Zalcitabine

Zudovudine or AZT

Representative of the 1,3-oxathiolane nucleosides is Lamivudine, an HIV reverse transcriptase inhibitor that is clinically indicated in combination therapy with Zidovudine, or with Abacavir and Zidovudine. The pyrimidine base of Lamivudine is attached in a cis relationship to the carbon atom at position 5 of the 1,3-oxathiolane ring. Lamivudine, which is marketed as a single enantiomer of (−)-2(R)-cis absolute configuration, displays pronouncedly enhanced antiviral properties relative its mirror image isomer.

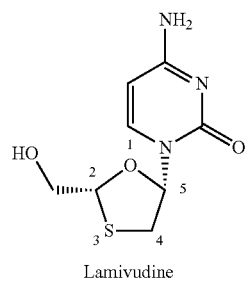

Lamivudine

Emtricitabine is a second representative of the 1,3-oxathiolane nucleosides that was developed as a treatment regimen for HIV infection. This drug is dispensed as a fixed-dose combination with Efavirenz, Emtricitabine and Tenofovir Disoproxil. Emtricitabine is a fluorinated analogue of Lamivudine with a (−)-2(R)-cis absolute configuration. The racemic form of Emtricitabine, known as FTC, is also under clinical development in combination with other approved anti-HIV drugs.

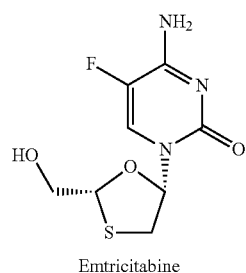 [SMILES: Nc1nc(=O)n([C@@H]2CS[C@H](CO)O2)cc1F]

Emtricitabine

Although the above nucleosides are constructive therapeutic regimens against HIV infection, many patients develop strains that become resistant to these drugs after prolonged periods of treatment. The sustained development of new anti- HIV drugs, therefore, remains a pivotal focus of the pharmaceutical industry. In this light, Apricitabine is currently undergoing clinical development and is showing very promising indications. Apricitabine has a mechanism of action similar to other nucleoside reverse transcriptase inhibitors making up the first-line therapies for treating HIV infection, but clinically this compound has exhibited the added benefits of a stronger safety profile, a broader activity profile against the difficult-to-treat, drug-resistant viruses, and a lower tendency to cause resistance in patients after prolonged treatment. Apricitabine has a 2(R)-cis absolute configuration, but in marked contrast to Lamivudine and Emtricitabine, the pyrimidine base in Apricitabine is attached to the 4-position of the 1,3-oxathiolane ring. Apricitabine is the first in class of a series of positional-switch 1,3-oxathiolane nucleosides that portray enhanced, broader spectrum anti-HIV activity.

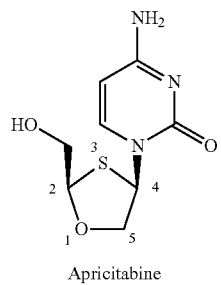 [SMILES: Nc1ccn([C@H]2CO[C@@H](CO)S2)c(=O)n1]

Apricitabine

Prior art teaches three processes for the preparation of 4-nucleobase-1,3-oxathiolanes. Common to each of these processes is a reaction of a purine or pyrimidine base with a compound of Formula II wherein $R_2$ may be a hydrogen or an acyl group, and wherein X may be a leaving group, a displaceable atom or an $NH_2$ group. Of consequence to the present invention may be optically pure 2-(acyloxymethyl)-1,3-oxathiolanes of Formula I. A Pummerer rearrangement of the latter may provide a compound of Formula II wherein $R_2$ may be an acyl group and X may be a carboxylate leaving group. As a result, optically pure compounds of Formula I may serve as valuable intermediates for manufacture of Apricitabine and other 4-nucleobase-1,3-oxathiolane antiviral derivatives.

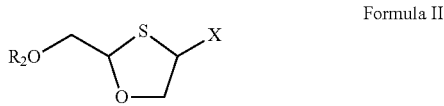

Formula II 2-(Acyloxymethyl)-1,3-oxathiolanes of Formula I may be prepared by oxidative cleavage of glycerol monoesters. The product of this reaction may be a glycolaldehyde ester, which when treated with 2-mercaptoethanol may generate a 2-(acyloxymethyl)-1,3-oxathiolane. This method may find restricted commercial viability because the acylation of glycerol may be non-selective and may yield a mixture of the primary and secondary mono-esters unless glycerol is first converted to solketal. Furthermore, glycolaldehyde esters tend to be unstable compounds, which may restrict their purification, storage and handling.

Additionally, glycolaldehyde esters may be prepared by (i) condensation of an acyl chloride with glycolaldehyde diethyl acetal, (ii) ozonolytic cleavage of 2-butene-1,4-diol diesters, and (iii) oxidation of a 2-(hydroxyethyl)carboxylates. The major limitations facing these processes may include (i) a low yield in the oxidation of 2-(hydroxyethyl)carboxylates, (ii) the instability of glycolaldehyde esters, and (iii) the specialized and costly facility required for conducting an ozonolysis at commercial scale.

In addition, a racemic compound of Formula I wherein $R_1$ is a phenyl group may be prepared in three steps from an alkali metal benzoate and a haloacetaldehyde acetal. In one such example, hydrolytic cleavage of 2-(benzoyloxy)acetaldehyde diethyl acetal may provide benzoyl glycolaldehyde and thence (+/−)-2-(benzoyloxymethyl)-1,3-oxathiolane upon acetalation with 2-mercaptoethanol. A major limitation of this process may be the instability of benzoyl glycolaldehyde. In an improvement upon this process, 2-(benzoyloxy)acetaldehyde diethyl acetal may be reacted with 2-mercaptoethanol directly to yield the 1,3-oxathiolane.

Prior art further teaches optically active, 1,3-oxathiolane nucleosides may be obtained by various techniques and methods including (i) asymmetric synthesis, (ii) chiral chromatography of a racemate, (iii) enzyme-mediated enantioselective catabolism, degradation or kinetic resolution, (iv) synthesis and separation of diastereomers derived from a chiral auxiliary, and (v) crystallization of diastereomeric salts.

An asymmetric synthesis of optically active, 5-nucleobase-1,3-oxathiolanes was reported wherein L-gulose may serve as the source of naturally occurring chirality. While interesting, this process may be restricted in scope and not easily extended to the production of optically active 4-nucleobase-1,3-oxathiolanes.

The separation of enantiomers by chiral chromatography may provide another avenue to optically active antiviral nucleosides. The compound of interest, or a convenient process intermediate such as a 2-(acyloxymethyl)-1,3-oxathiolane of Formula I, may be obtained in optically pure form by separation of the enantiomers on a suitably functionalized β-cyclodextrin, cellulose or amylose chromatographic medium using high performance liquid chromatography (HPLC) or simulated moving bed chromatography. While such processes may be scaled to commercial level, their utility may be constrained by the high cost of chiral chromatography relative to other methods of separating enantiomers, and by the lack of a recycle of the opposite enantiomer.

In addition, certain enzymes may be applied to resolutions of nucleoside derivatives. Emtricitabine may be obtained by a selective enzymatic degradation of a (+)-5'-monophosphate derivative with 5'-nucleotidase followed by alkaline phosphatase hydrolysis of (−)-5'-Emtricitabine phosphate. Enzyme-mediated enantioselective catabolism with cytidine-deoxycytidine deaminase may be utilized in a resolution of FTC. An immobilized cytidine-deoxycytidine deaminase enzyme was subsequently developed for this process. Additionally, enzymatic kinetic resolution of 5'-nucleoside carboxylates may be used in the synthesis of Emtricitabine. Pig liver esterase (PLE) may be applied to a resolution of FTC, and this process was scaled to the one hundred gram level. PLE may also be employed to resolutions of other 5'-nucleoside carboxylates. The resolution of 5'-FTC-carboxylates was further improved to yield Emtricitabine by employing an immobilized cholesterol esterase from *Candida cyclindracea*. The optical purity of Emtricitabine obtained by this process may be further enriched by recrystallization. The foremost limitation with each of the above enzymatic processes may be that the resolution step comes at or near the end of the synthetic pathway and the opposite enantiomer may be destroyed or not be easily racemized. With the aim of improving the economics of manufacture, one skilled in the art may prefer to conduct a resolution early in the manufacturing process. In this light, 2-(benzoyloxymethyl)-1,3-oxathiolane-4-propionate was screened against nine lipases and two proteases. The highest enantioselectivity (76%) and yield (14%) for the (−)-isomer was obtained with *Mucor miehei* lipase. The low yield and modest enantioselectivity of this process, unfortunately, may present significant impediments to its commercialization.

Moreover, optically pure isomers of compounds of Formulas I and II may be obtained from synthetic diastereomers incorporating (+)- and (−)-menthol as a chiral auxiliary. For example, the diastereomers of (1'R',2'S,5'R)-menthyl-1,3-oxathiolane-2-carboxylate may be prepared and separated by fractional crystallization, and a subsequent reduction of the individual diastereomers may afford optically pure 2(R)- or 2(S)-(hydroxymethyl)-1,3-oxathiolanes. Enantiomers of certain nucleosides may also be separated via chiral auxiliaries. Whilst these methods may be practical at research scale, they may find limited utility for large scale manufacture because (i) the chiral auxiliary may significantly add to the cost, and (ii) the process may not render a recycle of the opposite enantiomer.

Furthermore, certain 4-nucleobase-1,3-oxathiolane racemates may be resolved by diastereomeric salt formation and fractional crystallization. For example, cis-(−)-2-(hydroxymethyl)-4-(cytosine-1'-yl)-1,3-oxathiolane may be resolved by fractional crystallization of a salt formed between the racemate and (1R)-(−)-10-camphorsulphonic acid. The principle drawback of this process may be the resolution occurs at or near the final step of the synthesis wherein racemization and recycle of the opposite enantiomer may not be possible.

The present invention describes a new and superior process for manufacture of optically pure 2-(acyloxymethyl)-1,3-oxathiolanes of Formula I. Such compounds may be useful intermediates in the manufacture of optically active antiviral drugs such as Apricitabine.

II. SUMMARY OF THE INVENTION

According to one aspect of the present invention, a new and improved process is provided that may facilitate economical large-scale manufacture of optically pure 2-(acyloxymethyl)-1,3-oxathiolanes of Formula I and optically active 4-nucleobase-1,3-oxathiolanes.

One advantage of this invention over the prior art may be that the resolution of the racemate occurs early in the manufacturing process and provides a process intermediate to several optically active 4-nucleobase-1,3-oxathiolanes. The process may be used, therefore, to prepare a wide range of single enantiomer antiviral drugs.

Another advantage of this invention over prior art may be a racemization and recycle of the by-product of the enzymatic reaction so as to significantly increase the overall yield of the desired enantiomer from a racemic compound of Formula I.

Yet another advantage of this invention over prior art may be the scalability of an enzymatic process relative to prior art.

Still other benefits and advantages of the invention will become apparent to those skilled in the art to which it pertains upon a reading and understanding of the following detailed specification.

III. BRIEF DESCRIPTION OF THE FIGURES

The invention may take physical form in certain parts and arrangement of parts, a preferred embodiment of which will be described in detail in this specification and illustrated in the accompanying figures which form a part hereof and wherein.

IV. DETAILED DESCRIPTION OF THE INVENTION

Figure 1:
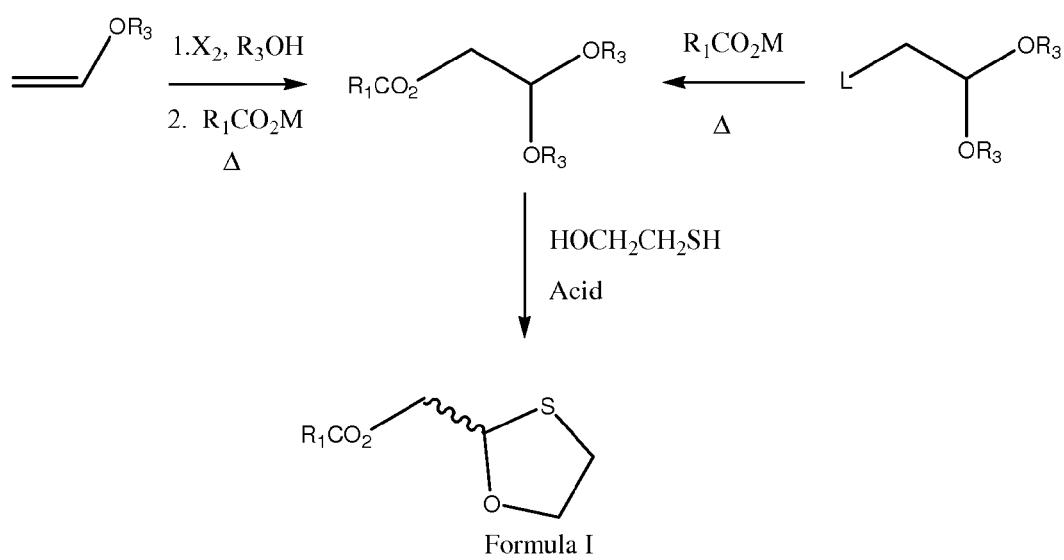
FIG. 1 is an illustration of two methods for preparation of racemic 2-(acyloxymethyl)-1,3-oxathiolanes of Formula I.

As referred to herein, the term "trans-acetalation" refers to the act of exchanging one of more of the alkoxy groups of an acetal with another heteroalkoxy or carboxylate group.

As referred to herein, the term "acylation" refers to the act of attaching an acyl group to a molecule.

As referred to herein, the term "acyl" represents a C(O) group that is attached by a carbon-carbon bond to alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl.

As referred to herein, the term "alkenyl" represents an unsaturated linear or branched carbon chain, comprised of at least one carbon-carbon double bond and 2-20 carbon atoms, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Useful examples of alkenyl may include, but are not limited to, 2-propenyl, 3-butenyl and isopropenyl.

As referred to herein, the term "alkyl" represents a saturated linear or branched carbon chain comprised of 1-20 carbon atoms that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Useful examples of alkyl may include, but are not limited to, methyl, ethyl, isopropyl, sec-butyl, t-butyl and n-hexyl.

As referred to herein, the term "alkynyl" represents an unsaturated linear or branched carbon chain, comprised of at least one carbon-carbon triple bond and 2-20 carbon atoms, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Useful examples of alkynyl may include, but are not limited to, propargyl, 2-butynyl and 4-pentynyl.

As referred to herein, the term "Apricitabine" refers to 2(R)-cis-4'-amino-1-[2-(hydroxymethyl)-1,3-oxathiolan-4-yl]-2(1H)-pyrimidinone, or as otherwise referred to in the chemical literature as SPD-754, or AVX-754, or (−)-BCH-10618.

As referred to herein, the term "aralkyl" represents an aryl attached to the adjacent atom by an alkyl. Useful examples may include, but are not limited to, benzyl and 2-phenethyl.

As referred to herein, the term "aryl" represents a cyclic moiety, comprised of at least one benzenoid-type carbon ring and 6-18 carbon atoms, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Useful examples of aryl may include, but are not limited to, phenyl, naphthyl and indenyl.

As referred to herein, the term "by-product" refers to a 2-(hydroxymethyl)-1,3-oxathiolane of Formula III of opposite absolute configuration relative to the desired enantiomer of the enzymatic resolution process.

As referred to herein, the term "chiral" refers to a compound that contains one or more carbon atoms, the chiral center, to which four different groups are bonded. The spatial orientation of the groups attached to a chiral carbon center may be defined in absolute terms as either R or S, wherein the priority assignment of each group may be defined by Cahn-Ingold-Prelog sequence rules.

As referred to herein, the terms "cis" and "trans" refers to the spatial orientation of two groups on a ring or a double bond. The spatial orientation may be defined as being cis whenever the groups are attached to the same face of the ring or double bond, and as being trans whenever the groups are attached to opposite faces of the ring or double bond.

As referred to herein, the term "cycloalkenyl" represents an unsaturated carbocycle, comprised of at least one carbon-carbon double bond and 5-16 carbon atoms, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Furthermore, cycloalkenyl may represent a monocycle or a polycycle. Useful examples of cycloalkenyl may include, but are not limited to, 3-cyclopentenyl, 1-cyclohexenyl, 2-cyclohexenyl, 3-cyclohexenyl and 1-cycloheptenyl.

As referred to herein, the term "cycloalkenyl-alkyl" represents a cycloalkenyl attached to the adjacent atom by an alkyl. Useful examples may include, but are not limited to, 3-cyclopentenyl-methyl and 1-cyclohexenylmethyl.

As referred to herein, the term "cycloalkyl" represents a saturated carbocycle comprised of 3-16 carbon atoms that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Furthermore, cycloalkyl may represent a monocycle or a polycycle. Useful examples of cycloalkyl may include, but are not limited to, cyclopropyl, cyclobutyl, cyclopentyl, cyclohexyl, norbornyl and adamantyl.

As referred to herein, the term "cycloalkyl-alkyl" represents a cycloalkyl attached to the adjacent atom by an alkyl. Useful examples may include, but are not limited to cyclopentylmethyl, cyclopropylmethyl and cyclobutylethyl.

As referred to herein, the term "diastereomer" refers to compounds that contain two or more chiral centers and the object compound is not the mirror image of the second compound. Unlike enantiomers, diastereomers may have different physical properties that may facilitate their separation by achiral techniques such as crystallization and chromatography.

As referred to herein, the term "electrophilic addition" refers to the act of adding one or more functional groups across a double bond wherein an incipient carbonation may be formed.

As referred to herein, the term "enantiomer" refers to the three-dimensional stereo-relationship between chiral molecules that are mirror image isomers. An enantiomer contains one or more chiral centers that impart a unique three-dimensional structure to the compound. Enantiomers have identical physical properties with the exception of their being able to rotate plane polarized light in equal amounts, but in opposite directions.

As referred to herein, the term "enantiomerically enriched" refers to a chiral compound that may be comprised of more than 50% of an enantiomer.

As referred to herein, the term "enzymatic kinetic resolution" refers to the act of selective catalysis by an enzyme of a reaction of one enantiomer over the other.

As referred to herein, the term "esterification" refers to the act of conversion of an alcohol group to an ester.

As referred to herein, the term "heteroaryl" represents a cyclic aromatic moiety comprised of 1-16 carbon atoms, wherein said ring contains at least one heteroatom selected from among oxygen, or sulfur, or nitrogen, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Furthermore, the heteroaryl may represent a monocycle or a polycycle. Useful examples of heteroaryl may include, but are not limited to, furan, benzofuran, isobenzofuran, pyrrole, imidazole, pyridine, pyrimidine, indole, thiophenene, quinoline and isoxazole.

As referred to herein, the term "heteroaryl-alkyl" represents a heteroaryl attached to the adjacent atom by an alkyl. Useful examples may include, but are not limited to, 2-thiophenylmethyl and 3-pyridylethyl.

As referred to herein, the term "heterocycloalkyl" represents a cyclic moiety comprised of 1-16 carbon atoms, wherein said ring contains at least one heteroatom selected from among oxygen, or sulfur, or nitrogen, that may optionally bear one or more substituents selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido. Furthermore, the heterocycloalkyl may represent a monocycle or a polycycle, and may contain one or more carbon-carbon double bonds within the cyclic moiety. Useful examples of heterocycloalkyl may include, but are not limited to, oxirane, aziridine, dihydrofuran, tetrahydrofuran, tetrahydropyran, pyrrolidine, piperadine, piperazine, oxathiolane, dithiolane, dioxolane, morpholine and thiomorpholine.

As referred to herein, the term "heterocycloalkyl-alkyl" represents a heterocycloalkyl attached to the adjacent atom by an alkyl. Useful examples may include, but are not limited to, 2-tetrahydrofuranylmethyl, 4-piperidinylmethyl and 2-pyrrolidinylethyl.

As referred to herein, the term "leaving group" or "L" refers to a substituent that is displaced from the carbon atom to which it was attached by a nucleophile during a nucleophilic substitution reaction or by a base during an elimination reaction. Useful examples of leaving groups may include, but are not limited to, chloro, bromo, iodo, hydroxy, mercapto, formate, acetate, trifluoroacetate, methanesulfonate, trifluoromethanesulfonate, ethanesulfonate, propanesulfonate, p-toluenesulfonate and p-nitrotoluenesulfonate.

As referred to herein, the term "nucleophile" refers to a group or atom that forms a chemical bond to its reaction partner by donating bonding electrons. Both neutral groups and negatively charged groups with a free pair of electrons may act as nucleophiles. Useful examples of nucleophiles may include, but are not limited to, iodide, hydroxyl, water, alkoxides, thioalkoxides, azide, ammonia, phthalimide and amines.

As referred to herein, the term "nucleophilic substitution reaction" refers to the act of displacing a leaving group from an sp$^3$-hydridized carbon atom with a nucleophile so as to produce a new chemical bond between the carbon atom and the nucleophile along with the formation of HL.

As referred to herein, the term "optically active" refers to a compound comprised of greater than 50% of an one enantiomer relative to the other enantiomer.

As referred to herein, the term "optically pure" refers to a 2-substituted-1,3-oxathiolane composition that may include more than about 90% of one enantiomer.

As referred to herein, the term "optionally" means (a) that a substituent may be the same or different definition for each item.

As referred to herein, the terms "racemate" or "racemic" refer to a chiral compound that is comprised of an equal mixture of the two enantiomers. A racemic compound does not rotate plane polarized light and often has different physical properties than that of an enantiomer.

As referred to herein, the term "racemization" refers to the act of converting a compound that is enantiomerically enriched in one enantiomer into a product that is of lower enantiomeric enrichment.

As referred to herein, the term "substituent" refers to a group that may be selected from among, but not limited to, fluoro, or chloro, or bromo, or iodo, or nitro, or nitroso, or sulfate, or sulfate ester, or sulfonate, or sulfonate ester, or phosphonate ester, or $C_{1-8}$ alkyl, or $C_{1-8}$ alkenyl, or $C_{1-8}$ alkynyl, or $C_{3-12}$ cycloalkyl, or $C_{5-12}$ cycloalkenyl, or $C_{6-18}$ aralkyl, or $C_{4-18}$ cycloalkyl-alkyl, or $C_{6-18}$ cycloalkenyl-alkyl, or heterocycloalkyl having 3-10 ring-members, or $C_{3-12}$ heterocycloalkyl-alkyl, or heteroaryl having 5-12 ring-members, or $C_{3-12}$ heteroaryl-alkyl, or $C_{6-18}$ aryl, or $C_{1-8}$ alkoxy, or $C_{6-18}$ aryloxy, or $C_{1-8}$ alkylmercapto, or $C_{6-18}$ arylmercapto, or acyl, or S(O)—$C_{1-8}$ alkyl, or S(O)—$C_{6-18}$ aryl, or S(O)—$C_{3-12}$ heteroaryl, or S(O)—$C_{3-12}$ heterocycloalkyl, or S(O)$_2$—$C_{1-8}$ alkyl, S(O)$_2$—$C_{6-18}$ aryl, or S(O)$_2$—$C_{3-12}$ heteroaryl, or S(O)$_2$—$C_{3-12}$ heterocycloalkyl, or hydroxy, or mercapto, or amino, or ester, or carboxylate, or carboxamide, or cyano, or azido.

Referring now to FIGS. 1-4, wherein the showings are for purposes of illustrating embodiments of the invention only and not for purposes of limiting the same, there is provided a process for preparation of (+/−)-2-(acyloxymethyl)-1,3-oxathiolanes of Formula I, resolution of the enantiomers by enzymatic kinetic resolution, and esterification and racemization of the by-product of the enzymatic resolution reaction. These embodiments may facilitate the manufacture of optically pure 2(R)- and 2(S)-(acyloxymethyl)-1,3-oxathiolanes. The so obtained products may be useful intermediates for manufacture of optically pure 4-nucleobase-1,3-oxathiolanes, including, but not limited to, Apricitabine.

I. Preparation of Racemic 2-(Acyloxymethyl)-1,3-Oxathiolanes

FIG. 1 illustrates two processes by which a racemic compound of Formula I may be prepared for use in the invention. Other methods for preparation of such racemates may be provided in the art. One process may employ a nucleophilic substitution reaction between a carboxylic acid salt of formula $R_1CO_2M$, wherein $R_1$ may be a group selected from among hydrogen, or alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, and wherein M may be an alkali metal ion such as lithium, or sodium, or potassium, or cesium, or an alkaline earth metal ion such as magnesium, or calcium, or barium, and a substituted acetaldehyde acetal of formula $LCH_2CH(OR_3)_2$, wherein L may be a halide such as chloride, or bromide, or iodide, or a sulfate derivative such as methanesulfonate, or trifluoromethanesulfonate, or benzenesulfonate, or para-toluenesulfonate, and wherein $R_3$ may be a group selected from among acyl, alkyl, or alkenyl, or alkynyl, or aralkyl, or aryl, or cycloalkenyl, or cycloalkenyl-alkyl, or cycloalkyl, or cycloalkyl-alkyl, or heteroaryl, or heteroaryl-alkyl, or heterocycloalkyl, or heterocycloalkyl-alkyl, to afford an intermediate having a formula of $R_1CO_2CH_2CH(OR_3)_2$. In the second reaction step, a trans-acetalation reaction with 2-mercaptoethanol may produce the (+/−)-2-(acyloxymethyl)-1,3-oxathiolane of Formula I.

The nucleophilic substitution reaction may be performed by heating the neat mixture, or by conduct of the reaction in a solvent system wherein a sufficient temperature may be achieved to drive the reaction to completion. Generally a polar, aprotic solvent such as N,N-dimethylformamide, or N-methylpyrrolidinone, or dimethyl sulfoxide may be favored; however, in certain instances the solubility of the reaction components may render itself to the use of other solvents, or solvent mixtures, such as acetone, or acetonitrile, or diisopropyl ether, or dioxane, or tetrahydrofuran, or methanol, or ethanol, or n-propanol, or isopropanol, or n-butanol, or sec-butanol, or tert-butanol, or n-pentanol, or isoamyl alcohol, or tert-pentanol, or toluene, or xylene, or mesitylene, or hexanes, or heptane.

In other instances, the nucleophilic substitution reaction may be performed in a two-phase system or a heterogeneous system. Moreover, in certain instances the reaction may be accelerated by inclusion of a phase transfer catalyst, such as Adogen® 464, or Aliquat® 100, or Aliquat® 336, or benzyltributylammonium chloride, or benzyltributylammon-ium iodide, or didecyldimethylammonium bromide, or hexadecyltrimethylammonium bromide, or hexyltributyl-phosphonium bromide-polymer-supported, or 18-crown-6, or dibenzo-18-crown-6. In other instances, the addition of sodium iodide, or potassium iodide, or cesium iodide may promote the substitution reaction.

The nucleophilic substitution reaction may be heated at a temperature of greater than 50° C., but less than 210° C. More generally, the reaction may be conducted at the reflux temperature of the solvent.

A carboxylate salt of formula $R_1CO_2M$ may be added directly to the reaction, or the salt may be generated in situ by addition of a metal hydroxide such as sodium hydroxide, or potassium hydroxide, or cesium hydroxide, or calcium hydroxide, or barium hydroxide, or magnesium hydroxide, or by a metal carbonate such as, sodium bicarbonate, or sodium carbonate, or potassium bicarbonate, or potassium carbonate, or cesium carbonate, or barium carbonate, or calcium carbonate, or magnesium carbonate hydroxide, to a carboxylic acid of formula $R_1CO_2H$.

The nucleophilic substitution product of formula $R_1CO_2CH_2CH(OR_3)_2$ may be isolated by aqueous work-up, or by concentration of the reaction solvent, or by crystallization, and purified by standard organic chemistry methods suitably tailored for the specific compound of interest including chromatography, distillation, crystallization, or treatment with carbon and filtration. In other instances, the product may be sufficiently pure to be carried directly into the next reaction step without purification.

In the second step, a trans-acetalation reaction between a compound of formula $R_1CO_2CH_2CH(OR_3)_2$ and 2-mercaptoethanol may be catalyzed by a mineral acid such as hydrochloric acid or sulfuric acid, or by an alkylsulfonic acid such as methanesulfonic acid or ethanesulfonic acid, or by an arylsulfonic acid such as phenylsulfonic acid or para-toluenesulfonic acid, or by a halogenated sulfonic acid such as trifluoromethanesulfonic acid, or by a Lewis acid such as boron trifluoride etherate, or tin tetrachloride, or titanium tetrachloride, or by a strongly acidic resin such as DOWEX® 50W, or DOWEX® DR-G8, or Amberlite®CG50, or Amberlite® CG120, Amberlite® IR120. In certain instances, the reaction may be driven by distillative removal of $R_3OH$, or by the addition of an excess quantity of 2-mercaptoethanol.

The trans-acetalation reaction may be conducted by heating a neat mixture of the reactants, or in a solution wherein a suitable solvent or mixed solvent system comprised of benzene, or toluene, or xylene, or mesitylene, or dioxane, or tetrahydrofuran.

The racemic compound of Formula I may be isolated and purified in an analogous manner as previously described for a compound of formula $R_1CO_2CH_2CH(OR_3)_2$. In other instances, the product may be sufficiently pure to be carried directly into the resolution step without purification.

In a second process of FIG. 1, an electrophilic addition of molecular halogen, wherein $X_2$ is chlorine, or bromine, or iodine, to a vinyl ether or vinyl ester of formula $CH_2=CH-OR_3$, and wherein $R_3$ may be defined as above, in the presence of $R_3OH$ may produce an intermediate of formula $LCH_2CH(OR_3)_2$, wherein L may be chloride, or bromide, or iodide. Heating this intermediate with a carboxylate salt of formula $R_1CO_2M$, wherein $R_1$ and M may be defined as above, may lead to a compound of formula $R_1CO_2CH_2CH(OR_3)_2$. An important advantage of the second process may be the cost savings achieved through use of vinyl acetate, vinyl benzoate or vinyl ethers ($CH_2=CH-OCH_3$, $CH_2=CH-OCH_2CH_3$) relative to halo acetaldehyde acetals.

Furthermore, the electrophilic addition reaction may be performed with N-bromosuccinimide, or N-chlorosuccinimide, or N-iodosuccinimide in place of the respective molecular halogen. In certain instances these reagents may offer ease of handling and selectivity differences relative to the molecular halogens.

Moreover, the electrophilic addition reaction may be performed directly in $R_3OH$ as a solvent system, or in the presence of a added co-solvent, selected from among acetone, or acetonitrile, or butyl acetate, or dichloromethane, or chloroform, or diethyl ether, or diisopropyl ether, or dioxane, or ethyl acetate, or ethyl propionate, or ethyl butyrate, methyl or tert-butyl ether, or tetrahydrofuran, or benzene, or toluene, or xylene, or mesitylene, or hexanes, or heptane.

The intermediate of formula $LCH_2CH(OR_3)_2$ may be isolated from the reaction and purified in an analogous manner to that described above for a compound of formula $R_1CO_2CH_2CH(OR_3)_2$, or in certain instances may be produced in sufficient purity to be used directly in the next step without purification, or in other instances may be converted in a subsequent step to a compound of formula $R_1CO_2CH_2CH(OR_3)_2$ without isolation.

In a further variant of this chemistry, in certain instances a three-component, simultaneous transformation may be achieved by reacting a vinyl ether or vinyl ester of formula $CH_2=CH-OR_3$ with a molecular halogen, or N-bromosuccinimide, or N-chlorosuccinimide, or N-iodosuccinimide, in the presence of a carboxylic acid of formula $R_1CO_2H$ whenever $R_3$ may be desired to be the same as $R_1C(O)$.

II. Enzymatic Kinetic Resolution of 2-(Acyloxymethyl)-1,3-Oxathiolanes

Figure 2:
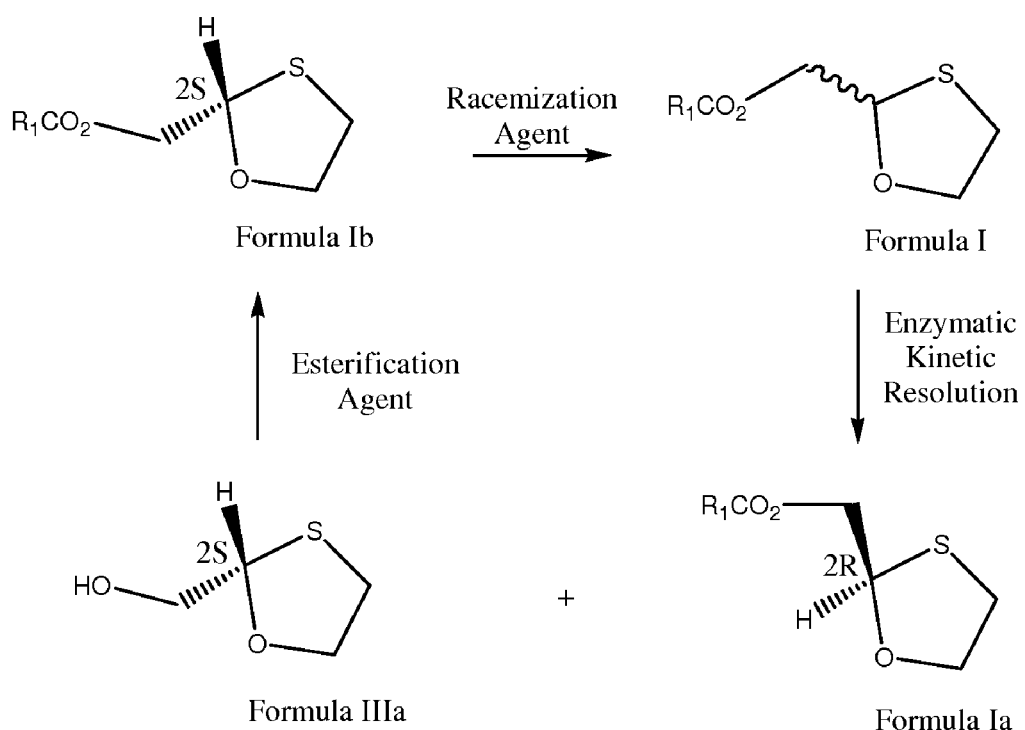
FIG. 2 is an illustration of a preferred process for resolution of optically pure 2(R)-(acyloxymethyl)-1,3-oxathiolanes of Formula Ia, and for esterification and racemization of the by-product of Formula IIIa of the enzymatic reaction.
Figure 3:
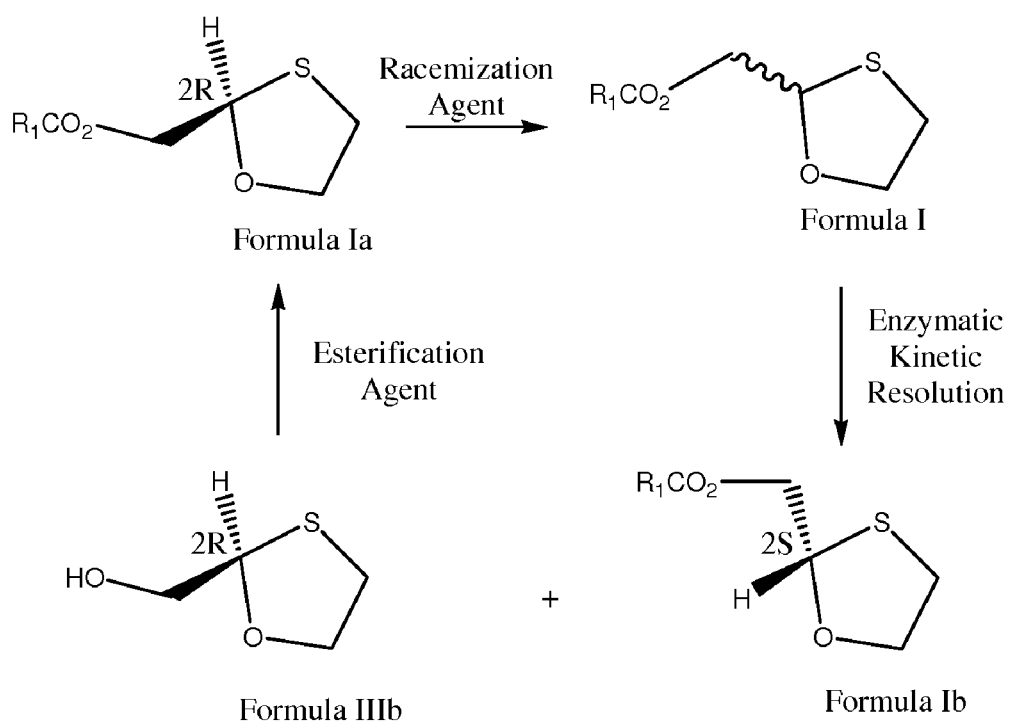
FIG. 3 is an illustration of a preferred process for resolution of optically pure 2(S)-(acyloxymethyl)-1,3-oxathiolanes of Formula Ib, and for esterification and racemization of the by-product of Formula IIIb of the enzymatic reaction.

In one embodiment of the invention, as shown in FIGS. 2 and 3, optically pure 2(R)- or 2(S)-(acyloxymethyl)-1,3-oxathiolanes of Formula Ia or Ib, wherein $R_1$ may be defined as above, may be obtained by enzymatic kinetic resolution. The method comprises the step of exposing a compound of Formula I to a hydrolytic enzyme that may preferentially catalyze a reaction of the undesired enantiomer. The technical breakthrough of the present invention relative to the prior art, may be the ability of an enzyme to recognize the enantiomers of a compound of Formula I based only on the subtle difference between an oxygen atom and a sulfur atom. In the prior art, the enzyme may benefit from two larger handles of recognition from which to differentiate between the enantiomers.

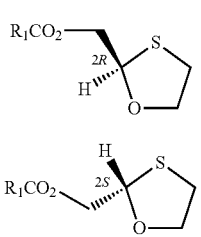

Formula Ia

Formula Ib

The substrate of the enzymatic resolution process may be a racemate or an enantiomerically enriched compound of Formula I. The optical purity of the substrate and the reaction product may be measured by chiral chromatography on an HPLC.

Furthermore, the hydrolytic enzyme may be an esterase, or a lipase, or a protease, or an acylase derived from a mammal, or a plant, or a bacterium, or a fungus, or yeast, or a virus, or an insect, or a reptile, or an amphibian. The hydrolytic enzyme may also be modified in its amino acid sequence or by non-sequence modification, or both. Wherein the hydrolytic enzyme may be isolated, it may be pure or used as a crude preparation. The hydrolytic enzyme may also be contained in a bacterial, or a fungal, or a yeast cell line rendering the process amenable to fermentation techniques. Moreover, the hydrolytic enzyme may be encoded and expressed in a vector or a suitable host cell line such as *E. coli*.

The enzymatic kinetic resolution reaction may be conducted with an enzyme that may be in solution, in suspension, or which may be immobilized on a solid support. Suitable solid supports for the enzyme may encompass, but need not be limited to, acrylate polymers, or agarose, or alumina, or buckyballs, or celite, or cellulose, or chitin, or dextran, or dendrimers, or Eupergit® C, or Eupergit® CM, or film, or glass, or nylon, or nitrocellulose, or plastic, or polyacrylamide, or polycarbonate, or polypropylene, or polystyrene, or pumice, or rubber, or sand, or silica, or silicon, or sol-gel polymer.

The enzymatic kinetic resolution reaction may be performed in a homogenous solvent system, or a two-phase system, or as an emulsion. Suitable solvents for the enzymatic reaction encompass aqueous buffer systems, or a mixed aqueous/organic solvent system comprised of one or more organic solvents selected from among, but not limited to, acetone, or acetonitrile, or n-butanol, or sec-butanol, or tert-butanol, or butyl acetate, or dichloromethane, or diethyl ether, or diisopropyl ether, or dimethyl sulfoxide, or dioxane, or ethanol, or ethyl acetate, or ethyl propionate, or ethyl butyrate, or isoamyl alcohol, or n-pentanol, or tert-pentanol, or methanol, of methyl tert-butyl ether, or tetrahydrofuran, or toluene, or xylene, or mesitylene, or hexanes, or heptanes.

The enzymatic kinetic resolution reaction may be performed in the presence of an inorganic or organic buffer selected from among, but not limited to, an acetic acid-acetate buffer, or a carbonate-bicarbonate buffer, or a citric acid-citrate buffer, or a glutamic acid-glutamate buffer, or a phosphoric acid-phosphate buffer, or a Tris-EDTA buffer, wherein the pH of the reaction medium may be maintained between about 2 and about 10, more preferably between about 4 and about 8, and most preferably between about 6 and about 7.5.

The by-product of the resolution process may be a compound of Formula III. In another embodiment of the invention, this by-product may be converted to a 2(R)- or 2(S)-(acyloxymethyl)-1,3-oxathiolane of Formula Ia or Ib by esterification methods described subsequently herein.

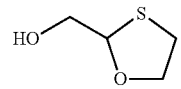

Formula III

In yet another embodiment of the invention, a compound of Formula III may be resolved by the addition of vinyl acetate, or vinyl benzoate, or butyl acetate to the reaction media so as to catalyze the reverse enzymatic reaction.

The products of the enzymatic kinetic resolution reaction may be separated by solvent partitioning, or crystallization, or distillation, or chromatography. The optical purity of the so obtained products may be further increased by recrystallization or chiral chromatography.

This embodiment of the invention may offer advantages over the prior art including, but not limited to, (i) a more economical and environmentally friendly process for production of compounds of Formula Ia and Ib, (ii) the ability to resolve enantiomers much earlier in the manufacture of optically active 4-nucleobase-1,3-oxathiolanes.

III. Esterification and Racemization of the By-Product of Formula III

In yet another embodiment of the invention, as shown in FIGS. 2 and 3, a two-step method may be provided for the esterification and racemization of the by-product of Formula III from the enzymatic reaction. A significant advantage of this embodiment is that recycle of the by-product may allow for a higher enzymatic conversion of substrate to the desired 2(R)- or 2(S)-(acyloxymethyl)-1,3-oxathiolane of Formula Ia or Ib. Recycle of the optical antipode may not be practical in processes previously reported in the art.

Within this embodiment, the by-product from the enzymatic reaction, a 2(R)- or 2(S)-(hydroxymethyl)-1,3-oxathiolane of Formula III, may be isolated using conventional organic chemistry techniques by one skilled in the art. This by-product typically may be contaminated with more than 1%, but less than about 50%, of the opposite enantiomer.

The by-product of Formula III may be esterified by reaction with a carboxylic acid chloride, $R_1COCl$, or a carboxylic acid anhydride, $(R_1CO)_2O$, or a mixed anhydride prepared from the carboxylic acid, $R_1CO_2H$, wherein $R_1$ may be defined as above. An appropriate base may be added to the reaction selected from among, but not limited to, sodium hydroxide, or potassium hydroxide, or triethylamine, or diisopropylethylamine, or pyridine, or N,N-dimethylaminopyridine. The reaction may be performed in an aqueous solvent system, or in a mixed aqueous and organic solvent system, or in one of more organic solvents selected from among, but not limited to, acetone, or acetonitrile, or hexanes, or heptanes, or butyl acetate, or dichloromethane, or chloroform, or diethyl ether, or diisopropyl ether, or dioxane, or ethyl acetate, or ethyl propionate, or ethyl butyrate, or methyl tert-butyl ether, or tetrahydrofuran, or toluene, or xylene, or mesitylene.

Alternative acylation systems may also be used in the esterification step and include (i) diethyl azodicarboxylate, triphenylphosphine and $R_1CO_2H$, (ii) dicyclohexylcarbodiimide and $R_1CO_2H$, or (iii) carbonylimidazole and $R_1CO_2H$. The product of the esterification reaction may be purified by crystallization, distillation or chromatography as appropriate for the specific product.

In a second reaction step of this embodiment, the chiral center in the so obtained optical antipode may be racemized. The racemization reaction may be catalyzed by an acid selected from among, but not limited to, those previously described for use in the trans-acetalation reaction of a compound of formula $R_1CO_2CH_2CH(OR_3)_2$. Furthermore, the reaction may be conducted by heating a neat solution of the 2-(acyloxymethyl)-1,3-oxathiolane with an acid, or by heating the reaction components in a suitable solvent selected from among, but not limited to, benzene, or toluene, or xylene, or mesitylene, or dioxane, or tetrahydrofuran. The racemized product may be isolated and purified in an analogous manner as described above, or in certain instances may be obtained in sufficient purity to be used directly in a subsequent resolution step. The extent of racemization may be measured by chiral HPLC.

In yet a further embodiment of the invention, a method is provided for a one-pot esterification and racemization of the by-product comprised of treating said by-product of Formula III with an acid catalyst in the presence of $R_1CO_2H$, wherein a Fischer esterification reaction may proceed concurrently with racemization of the acetal center. This embodiment may provide the added advantage of a single step transformation in the esterification and racemization of the by-product from the enzymatic process.

IV. Manufacture of
2-(Hydroxymethyl)-4-Nucleobase-1,3-Oxathiolanes

Figure 4:
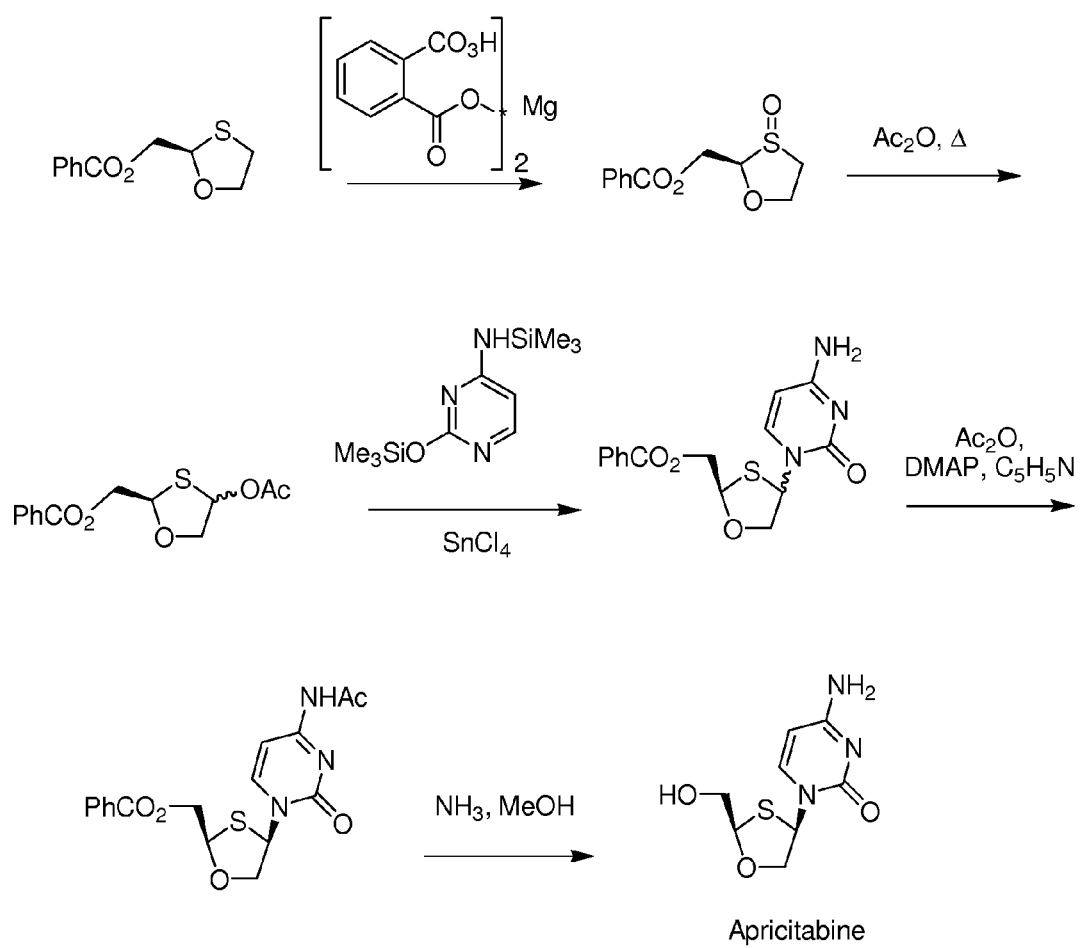
FIG. 4 is an illustration of a method for production of Apricitabine from a 2(R)-(acyloxymethyl)-1,3-oxathiolane of Formula Ia.

In yet another embodiment of the invention, the optically pure 2(R)-(acyloxymethyl)-1,3-oxathiolanes produced by the enzymatic kinetic resolution method described herein, may be valuable intermediates for manufacture of therapeutically valuable, 2(R)-cis nucleosides of Formula IV. For example, Apricitabine, as shown in FIG. 4, may be produced by treating optically pure 2(R)-(benzoyloxymethyl)-1,3-oxathiolane produced by the invention with a peracid to give a 2(R)-(benzoyloxymethyl)-1,3-oxathiolane sulfoxide, which upon treatment with acetic anhydride may yield 2(R)-(benzoyloxymethyl)-4-acetoxy-1,3-oxathiolane. The latter intermediate may be reacted with N,O-bis(trimethylsilyl)cytosine in the presence of tin tetrachloride to yield a mixture of the 2(R)-cis and 2(R)-trans-nucleoside derivatives. Treatment of this mixture with acetic anhydride may achieve a higher ratio of the desired cis isomer. Separation of the isomers may then give 2(R)-cis-O-benzoyl-N-acetyl-Apricitabine. Reaction with ammonia in methanol may remove the protecting groups and afford Apricitabine.

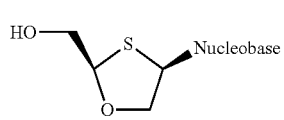

Formula IV

The following examples illustrate the present invention in a way that it may be practiced, but as such these examples should not be interpreted as limitations upon the overall scope of the methods of this invention.

Example 1

Preparation of 2-(Benzoyloxy)acetaldehyde Diethyl Acetal

To a 2-L, three-necked, round-bottomed flask fitted with a mechanical stirrer, a reflux condenser and a glass stopper is added sodium benzoate (0.579 mol, 83.44 g, 1.1 equiv.), bromoacetaldehyde diethyl acetal (0.526 mol, 103.74 g, 1.0 equiv.) and N,N-dimethylformamide (1.0 L). The reaction was heated to reflux and stirred while monitoring progress by thin layer chromatography (TLC). When determined to be complete, the reaction was allowed to cool to ambient temperature and diluted with water (2.0 L). The product was extracted with methyl tert-butyl ether. The organic phase was dried over magnesium sulfate and concentrated by rotary evaporation to give 2-(benzyloxy)acetaldehyde diethyl acetal (111.85 g, 81.1% yield). The crude product was advanced to the next reaction step without further purification.

Example 2

Preparation of (+/−)-2-(Benzoyloxymethyl)-1,3-Oxathiolane

To a 5-L, three-necked, round-bottomed flask fitted with a mechanical stirrer, a Dean-Stark apparatus, and a glass stopper is added 2-(benzoyloxy)acetaldehyde diethyl acetal (0.469 mol, 111.85 g, 1.0 equiv.), 2-mercaptoethanol (0.516 mol, 40.34 g, 1.1 equiv.), para-toluenesulfonic acid monohydrate (0.047 mol, 8.92 g, 0.1 equiv.) and toluene (3.5 L). The reaction was heated to reflux and stirred while monitoring progress by TLC. When determined to be complete, the reaction was allowed to cool to ambient temperature before washing with saturated sodium bicarbonate solution. The organic phase was dried over magnesium sulfate and concentrated by rotary evaporation to give (+/−)-2-(benzoyloxymethyl)-1,3- oxathiolane as an oil (95.75 g, 90.9% yield). The crude product was advanced to the next reaction step without further purification.

Example 3

Enzymatic Kinetic Resolution of (+/−)-2-(Benzoyloxymethyl)-1,3-Oxathiolane (+/−)-2-(Benzoyloxymethyl)-1,3-oxathiolane (0.71 mmol, 160 mg) was dissolved in acetonitrile (0.6 mL) in a 25-mL round-bottomed flask. A 0.1 M phosphoric acid-phosphate buffer solution (15 mL) adjusted to pH 7.0 was added to the reaction followed by 21 units of cholesterol esterase from bovine pancreas (Sigma #C3766). The reaction was stirred at approximately 4° C. for a period of up to 24 h while maintaining the pH of the reaction media at pH 7.0 with 1 M sodium hydroxide solution. The progress of the reaction may be monitored by gas chromatography for disappearance of the (+/)-2-(benzoyloxymethyl)-1,3-oxathiolane and/or by chiral HPLC for enantiomeric enrichment. When the reaction had proceeded to about 50% conversion, the mixture was saturated with sodium chloride and extracted with methyl tert-butyl ether (5×5 mL). Concentration of the extracts afforded a crude product that was purified by silica gel chromatography to give 2(R)-(benzoyloxymethyl)-1,3-oxathiolane (68 mg) and 2(S)-(hydroxymethyl)-1,3-oxathiolane (38 mg).

Example 4

Esterification of 2(S)-(Hydroxymethyl)-1,3-Oxathiolane

2(S)-(Hydroxymethyl)-1,3-oxathiolane (0.25 mmol, 30 mg, 1.0 equiv.) recovered from Example 3 was treated with benzoyl chloride (0.25 mmol, 35 mg, 1.0 equiv.), triethylamine (0.25 mmol, 25 mg, 1.0 equiv.) in dichloromethane (1 mL) at ambient temperature while monitoring the reaction progress by TLC. After 1 h, the reaction was extracted with saturated ammonium chloride solution and brine. The organic phase was concentrated and chromatographed on silica gel to give 2(S)-(benzoyloxymethyl)-1,3-oxathiolane (25 mg, 44.6%).

Example 5

Racemization of 2(S)-(Benzoyloxymethyl)-1,3-Oxathiolane

2(S)-(Benzoyloxymethyl)-1,3-oxathiolane (0.045 mmol, 10 mg, 1.0 equiv.), para-toluenesulfonic acid monohydrate (0.015 mmol, 3 mg, 0.3 equiv.) and toluene (1 mL) were heated to reflux and stirred while monitoring the racemization reaction by chiral HLPC. After 24 h, the reaction was allowed to cool to ambient temperature and washed with saturated sodium bicarbonate solution. The organic phase was dried over magnesium sulfate and concentrated by rotary evaporation to give 8 mg (80% yield) of (+/−)-2-(benzoyloxymethyl)-1,3-oxathiolane.

A number of embodiments and representative examples have been described, hereinabove. It will be apparent to those skilled in the art that there may be many alternatives, modifications and variations of these embodiments without departing from the general scope of this invention. This invention is intended to include all such modifications and alterations in so far as they come within the scope of the appended claims or the equivalents thereof.

Having thus described the invention, it is now claimed:

1. A process for esterification and racemization of a 2(S)-(hydroxymethyl)-1,3-oxathiolane compound of Formula IIIa;

Formula IIIa or a 2(R)-(hydroxymethyl)-1,3-oxathiolane compound of Formula IIIb;

Formula IIIb comprising the steps of:
(i) an esterification reaction of said compound of Formula IIIa or said compound of Formula IIIb with an esterification agent, so as to generate a 2(S)-(acyloxymethyl)-1,3-oxathiolane compound of Formula Ib

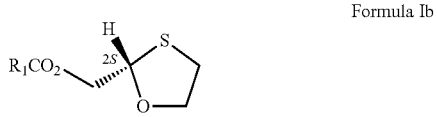

Formula Ib or a 2(R)-(acyloxymethyl)-1,3-oxathiolane compound of Formula Ia

Formula Ia where $R_1$ is a group selected from among hydrogen, alkyl, alkenyl, alkynyl, aralkyl, aryl, cycloalkenyl, cycloalkenyl-alkyl, cycloalkyl, cycloalkyl-alkyl, heteroaryl, heteroaryl-alkyl, heterocycloalkyl, or heterocycloalkyl-alkyl and
(ii) an acid-mediated racemization of said compound of Formula Ia or said compound of Formula Ib yielding a compound of Formula I of lower enantiomeric enrichment than said compound of Formula Ia or said compound of Formula Ib.

Formula I

2. The process of claim 1, wherein said compound of Formula IIIa or said compound of Formula IIIb contains about 50% to about 100% of an enantiomer of said compound of Formula IIIa or said compound of Formula IIIb.

3. The process of claim 1, wherein said esterification agent is an acid chloride of formula $R_1C(O)Cl$, an acid anhydride of formula $(R_1CO)_2O$, or a mixed acid anhydride prepared from $R_1CO_2H$, where $R_1$ is a group selected from among hydrogen, alkyl, alkenyl, alkynyl, aralkyl, aryl, cycloalkenyl, cycloalkenyl-alkyl, cycloalkyl, cycloalkyl-alkyl, heteroaryl, heteroaryl-alkyl, heterocycloalkyl, or heterocycloalkyl-alkyl.

4. The process of claim 1, wherein said esterification agent is comprised of a dialkyl azodicarboxylate, triarylphosphine and $R_1CO_2H$, a dialkylcarbodiimide and $R_1CO_2H$, a dicycloalkylcarbodiimide and $R_1CO_2H$, or carbonyldiimidazole and $R_1CO_2H$, where $R_1$ is a group selected from among hydrogen, alkyl, alkenyl, alkynyl, aralkyl, aryl, cycloalkenyl, cycloalkenyl-alkyl, cycloalkyl, cycloalkyl-alkyl, heteroaryl, heteroaryl-alkyl, heterocycloalkyl, or heterocycloalkyl-alkyl.

5. The process of claim 3 or claim 4, wherein $R_1$ bears at least one substituent.

6. The process of claim 3 or claim 4, wherein $R_1$ contains 6 to 12 carbon atoms and where $R_1$ is aryl.

7. The process of claim 3 or claim 4, wherein $R_1$ contains 1 to 12 carbon atoms and where $R_1$ is alkyl.

8. The process of claim 1, wherein a base is added to said esterification reaction.

9. The process of claim 1, wherein said esterification reaction is performed in an aqueous solvent, in a mixture of an aqueous solvent and one or more organic solvents, or in one or more organic solvents.

10. The process of claim 1, wherein said compound of Formula Ia or said compound of Formula Ib contains between about 50% and about 100% of said enantiomer.

11. The process of claim 1, wherein said racemization agent is an acid or a strongly acidic resin.

12. The process of claim 1, wherein said racemization is conducted in an organic solvent or performed neat.

13. The process of claim 1, wherein said compound of Formula Ia or said compound of Formula Ib is produced by a method other than esterification reaction of said compound of Formula IIIa or said compound of Formula IIIb, and converted to a compound of Formula I by a racemization agent.

14. The process of claim 1, wherein said compound of Formula I is a racemate, or contains 50 to 95 percent of said compound of Formula Ia or said compound of Formula Ib.

15. The process of claim 1, wherein said esterification and said racemization are performed concurrently by treating said compound of Formula IIIa or said compound of Formula IIIb with an acid in the presence of $R_1CO_2H$ where $R_1$ is a group selected from among hydrogen, alkyl, alkenyl, alkynyl, aralkyl, aryl, cycloalkenyl, cycloalkenyl-alkyl, cycloalkyl, cycloalkyl-alkyl, heteroaryl, heteroaryl-alkyl, heterocycloalkyl, or heterocycloalkyl-alkyl.

* * * * *